United States Patent [19]

Chan et al.

[11] Patent Number: 5,075,058

[45] Date of Patent: Dec. 24, 1991

[54] PROCESS FOR PREPARING PELLETS COMPRISING INSECTICIDAL N-HYDROCARBOYL PHOSPHOROAMIDOTHIOATES AND/OR PHOSPHOROAMIDODITHIOATES, AND FUNGICIDES, HERBICIDES, FERTILIZERS OR OTHER INSECTICIDES

[75] Inventors: Jim H. Chan, Martinez; Kent A. Hasse, El Sobrante; Roderick I. Satre, Point Richmond; James H. Trusler, Pleasant Hill, all of Calif.

[73] Assignee: Chevron Research and Technology Company, San Francisco, Calif.

[21] Appl. No.: 472,353

[22] Filed: Jan. 30, 1990

[51] Int. Cl.$^5$ ............................................. B29B 9/08
[52] U.S. Cl. ................................... 264/118; 264/141; 424/405; 424/408; 424/489; 514/120
[58] Field of Search ............... 264/118, 141, 142, 143, 264/117; 71/64.04; 424/408, 489, 405; 514/120

[56] References Cited

U.S. PATENT DOCUMENTS

| | | | |
|---|---|---|---|
| 3,914,417 | 10/1975 | Magee | 514/120 |
| 4,048,268 | 9/1977 | Ludwig | 264/118 |
| 4,374,082 | 2/1983 | Hochschild | 264/129 |
| 4,446,086 | 5/1984 | Molenaar et al. | 264/118 |
| 4,542,162 | 9/1985 | Rutherford et al. | 521/79 |
| 4,636,343 | 1/1987 | Shibanai | 264/118 |
| 4,665,100 | 5/1987 | Ludwig | 514/778 |
| 4,668,455 | 5/1987 | Hansen et al. | 264/143 |
| 4,678,594 | 7/1987 | Parfomak et al. | 264/118 |
| 4,683,224 | 7/1987 | Fahmy | 514/120 |
| 4,722,815 | 2/1988 | Shibanai | 264/117 |
| 4,767,773 | 8/1988 | Ayad | 514/351 |
| 4,769,242 | 9/1988 | Shibanai | 424/411 |

*Primary Examiner*—Mary Lynn Theisen
*Attorney, Agent, or Firm*—Heller, Ehrman, White & McAuliffe

[57] ABSTRACT

A method of making insecticidal pellet compositions of N-hydrocarboyl phosphoroamidothioates and phosphoroamidodithioates, combined with a herbicide, fungicide, fertilizer or other insecticide is provided.

11 Claims, No Drawings

PROCESS FOR PREPARING PELLETS COMPRISING INSECTICIDAL N-HYDROCARBOYL PHOSPHOROAMIDOTHIOATES AND/OR PHOSPHOROAMIDODITHIOATES, AND FUNGICIDES, HERBICIDES, FERTILIZERS OR OTHER INSECTICIDES

The present invention is directed to a method of making pelletized insecticidal N-hydrocarboyl phosphoroamidothioates and/or and phosphoroamidodithioate formulations containing fungicides, herbicides, fertilizers or other insecticides.

BACKGROUND OF THE INVENTION

Certain N-hydrocarboyl phosphoroamidothioates and phosphoroamidodithioates have high insecticidal activity. A particularly important commercial insecticide within these classes of compounds is the insecticide ORTHENE®, which can be systemically taken up by a plant so that insects which feed and/or live on the plant are killed, in addition to those insects which directly ingest or are contacted by the insecticide. See U.S. Patent Nos. 3,716,600, 3,845,172 and 3,914,417. ORTHENE® is commercially produced as technical grade chemical of about 97 to 99.5% purity. One method of formulating technical grade ORTHENE® for commercial use is to mix the technical grade powder with an anti-caking agent, such as fumed silica, and a wetting agent. The wetting agent is utilized to assist the wetting of silica (if present) and to improve the spread-out of ORTHENE® and the anti-caking agent is used to prevent agglomeration of the ORTHENE® in its container.

The wetting agent is utilized to assist the wetting of silica (if present) and to improve the spread-out of ORTHENE® when it is applied to crops as a spray solution, or when applied as a dust, after exposure to moisture via rain, dew, or irrigation. The powdered commercial forms of ORTHENE® are available in dilutions referred to as ORTHENE® 90S, ORTHENE® 75S, ORTHENE® 50S, and in other commercial dilutions.

The powder form allows formulations of ORTHENE® to relatively high concentrations, e.g., ORTHENE® 90S. Other, lower concentrate formulations are targeted to discrete markets using a soluble powder signified as -xxS. In most cases, the application of ORTHENE® XXS to the crop is via a water solution spray. The anti-caking agents, while promoting product flowability during the solution/mixing process, do not enhance the solution method of application. On the other hand, inherent to all powders, handling difficulties due to dust make this form of product less desirable than liquids and agglomerate forms. Furthermore, ORTHENE® has a characteristically mercaptan odor (believed to be organothio compounds) which is compounded by the problems with dust.

ORTHENE® is available in liquid form, which minimizes or eliminates airborne contamination due to dust. However, due to solubility and storage stability limitations of solutions, its concentration is limited to a maximum of 25%, the balance being solvent and adjuvants. ORTHENE® in a liquid formulation has a solvent and packaging expense as well as a container disposal requirement that makes it less attractive to the consumer on the basis of price and empty container disposal requirements.

An agglomerate form of ORTHENE® which also minimizes airborne contamination due to dust, has been constrained to dilute concentrations of ORTHENE® applied to large particles by spraying and then dried, or as a dilute concentration of ORTHENE® combined with binders and anti-caking agents to form agglomerates via processes known to those skilled in the art, such as, pan granulation, extrusion, fluid granulation, pelletizing. The concentration of ORTHENE® via these methods has heretofore been limited to a concentration no greater than about 36% to 50%, with known commercial products typically no more than 5% ORTHENE. The limit on concentration of ORTHENE® was due to the melt property of ORTHENE® limiting the feasible operability of this form of product. Concentration of active ingredient is further limited by the ability of binding agents to form agglomerates, i.e. a minimum amount of any particular binding agent is required in order to meet physical properties of attrition resistance, crush strength and bulk density. In the case where liquid ORTHENE® solutions were sprayed on agglomerates and then dried, the limitation of concentration was due to the practical wetting ability of the receiving agglomerate. Too much liquid applied would form a mud. At these low levels of ORTHENE® concentration, commercial products are more costly to produce and are not suitable for applications of ORTHENE® made via solution spraying.

The ORTHENE® xxS formulations have problems due to the inorganic anti-caking agent ingredients. These anti-caking agents are not soluble in water (the typical application spray solvent) or other normal solvents. Due to their insolubility, they can settle in the applicator's spray tank. The settled anti-caking agents plug spray nozzles which detracts from the marketability of the ORTHENE® xxS product line. This spray nozzle plugging problem can occur when ORTHENE® xxS products are tank mixed with other commercial pesticides, which is a normal farming industry practice. While methods to minimize the occurrence of anti-caking agent settling have evolved, they require special procedures to avoid nozzle plugging conditions, which adds to the inconvenience of using ORTHENE® xxS.

Furthermore, an anti-caking agent(s) segregates in the manufacturing process equipment during material handling procedures and forms insoluble bits of anti-caking agent which can cause spray nozzle plugging. This may lead to inconsistent application of the correct amount of active ingredient.

Therefore, alternative forms to ORTHENE® powders, that resolve problems characteristic of dusts are desired by both the manufacturer and the marketplace. One possible alternative to a powdered ORTHENE® is in the form of a pellet: a cylindrically shaped solid. Pellets practically eliminate the dust problems and reduce the surface area-to-weight ratio which mitigates the odor problem.

However, currently available granular ORTHENE®, as mentioned above, contains relatively small amounts of ORTHENE®, typically no more than 5% active ingredient. Attempts to manufacture technical assay (approximately 97% active ingredient) ORTHENE® pellets from the dry ORTHENE® technical powder have heretofore been unsuccessful. The anti-caking agents and binders needed to make the currently available granular ORTHENE® add to product cost, can cause excess wear and tear on equipment, and by dint of being a major fraction of the product formula, require more bulk product than the concentrated powders in order to deliver effective amounts of ORTHENE® to the protected crop.

Additionally, the anti-caking agents and binders used to form the currently available granular ORTHENE® have the same water insolubility problem that the anti-caking agent has in ORTHENE® powdered formulae. Because of that, commercial granular ORTHENE® products are limited to use by direct application to the crop; i.e., placing granules on or around each plant, which is impractical for most commercial farming ventures. Furthermore, occasionally there are compatibility problems in tank mixes containing ORTHENE® and other pesticides. It would thus be desirable to develop compatible cocktails of pesticides or mixes of pesticides with fertilizers.

It would therefore be desirable to provide a method for making pellets containing ORTHENE® as well as other fertilizers, herbicides, fungicides or even other insecticides for delivery of these active ingredients without the above problems.

It is thus an object of the present invention to provide pelletized forms of insecticidal N-hydrocarboyl phosphoroamidothioates and phosphoroamidodithioates containing fertilizers, herbicides, fungicides, or other insecticides.

This and other objects of the invention will be apparent from the following description and from the practice of the invention.

SUMMARY OF THE INVENTION

The present invention provides a method for preparing pelletized insecticidal compositions comprising pellets which contain as one of the active ingredients, an insecticidal compound or mixture of compounds of the formula:

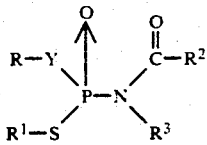

wherein R and R¹ individually are alkyl, alkenyl or alkynyl of up to 6 carbon atoms, R³ is hydrogen or alkyl of 1-6 carbon atoms, R² is hydrogen, alkyl of 1-18 carbon atoms, cycloalkyl of 3-8 carbon atoms, alkenyl of 2-18 carbon atoms or alkynyl of 3-18 carbon atoms, and Y is oxygen or sulfur. The pellets are characterized by an attrition resistance of at least about 92%, a mean hardness of greater than about 1.5 lb-F and a bulk density of at least about 39 lb/ft³ (about 0.63 gm/cc). The pellets are made by extrusion of a solid composition. The concentration of the insecticidal ingredient in these pellets is in the range of about 2% to 80% a.i., with the most likely concentration of 70% a.i.

DESCRIPTION OF THE PREFERRED EMBODIMENTS

One of the active insecticidal ingredient of the pellets will be a compound or a mixture of compounds of the formula:

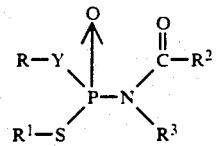

wherein R, R¹, R², R³ and Y are as described hereinabove. Particularly preferred compounds are those in which R and R¹ are independently methyl, ethyl, allyl or alkenyl; R² is H or alkyl; and R³ is hydrogen; and Y is oxygen. The most preferred compound is that in which R, R¹, and R² are methyl, R³ is hydrogen and Y is oxygen. Compounds of the above formula may be prepared as described in technical form in U.S. Pat. Nos. 3,716,600, 3,845,172 and 3,914,417 which usually provide compositions of about 97-98.5% purity. This technical grade insecticide will be mixed in a dry form with one or more solid or liquid active ingredients prior to being pelletized as described herein.

The mixture described above may also contain inert diluents, such as ammonium sulfate, in an amount less than about 5% by weight of the total pellet composition, preferably 2% or less by weight of the total pellet composition.

Surfactants may also be added, such as polymeric surfactants known by the trade names "Pluronic®" or "Tetronic®" (sold by BASF). Usually, less than about 5% by weight of the total pellet composition may comprise a surfactant. The surfactants used in accordance with the present invention are polymeric and, in order to form an extrudable solid composition, should be softenable within the temperature range of about 80. to 130.F and have melting points greater than about 130 F. Such nonionic surfactants include the generic types alkyl or aryl alcohol ethylates. These surfactants are commercially available under the trade names Unithox ™ (520, 580, 480 etc.) made by Petrolite Chemical; Pluronic® (BASF), Sellogen ™ (Henkel), Tetronic® surfactants, block copolymers of propylene and ethylene oxides of ethylenediamine; and Alkasurf ™, Alkatronic ™, Alkapol ™ (glycols) made by Alkaril Chemicals.

The particular surfactant used will depend in part on the intended use of the pellets. Those surfactants having an HLB in the range of about 16 to greater than 20 will be substantially water soluble and therefore be usable in conventional mixing tanks used to distribute sprays. Pellets made from surfactants having an HLB lower than about 16 will have lower water solubility and will be useful, for example, in direct application on the plants or their environment for controlled release of the active ingredients of the pellet.

Particularly preferred surfactants for imparting high water solubility to the pellets are Unithox 480. Particularly preferred surfactants for imparting low solubility to the pellets are Unithox 520.

It will be appreciated that combinations of different surfactants may also be utilized to modify the solubility properties of the pellet as desired.

Optionally, solid and/or liquid additives may be included in the dry mixture. Additives may include anhydrous magnesium sulfate, in amount up to about 5% by weight of the total pellet composition, preferably 2% or less by weight. This serves as a dehydrating agent and will absorb trace amounts of water present in the pellets to prevent hydrolysis of the insecticide. Small amounts of deodorants and anti-foam agents may also be used as additives.

As discussed above, it is a particular advantage of the present invention to provide pelletized compositions which contain active ingredients in addition to the insecticidal composition described above. In particular, it will particularly advantageous to combine the ORTHENE® insecticides in a pellet with other insecticides, particularly pyrethroid insecticides such as DECIS TM (also known as deltamethrin, melting point 98°–101°C.), PYDRIN TM and ASANA TM (Fenvalerate), DANITOL TM, CASCADE TM (Flufenoxuron), DURSBAN TM (chlorpyrifos), DIBROM TM ("Naled"), etc. Most of these insecticides are solids, thus to prepare a pellet with ORTHENE® they are preferably milled, if necessary, to fine particle grain size (1–8 microns average diameter), and mixed with a solid dispersant, solid wetting agent, and/or solid surfactant. A particularly preferred composition is a mixture of 13:1 ORTHENE® to ASANA TM containing 6% by weight of Morwet TM D425 dispersant; 0.5% wetting agent and 7% Unithox TM 480 surfactant formed into pellets.

Some of the above insecticides are liquids, such as PYDRIN TM (yellow liquid, melting point 23° C.). In such cases the liquid may be first absorbed onto a carrier such as a diatomaceous earth (such as Celatom TM) and then the two solids (the ORTHENE® and the PYDRIN TM saturated Celatom TM) may be mixed with a solid dispersant, solid wetting agent and solid surfactant.

In some instances, the second insecticide, such as DANITOL TM is highly toxic and therefore to alleviate the hazard of handling the pellets, the DANITOL TM may first be encapsulated by mixing with a surfactant such as Pluronic® series (F-108) Tetronic TM series (such as 908), Unithox TM series (such as 480, 550 or 520) by milling the DANITOL TM with the surfactant. The ORTHENE® is then mixed with the milled DANITOL TM/surfactant and pelletized in a pellet mill.

Similarly, solid or liquid fungicides, herbicides, or fertilizers may be pelletized with the ORTHENE® in accordance with the methods described above.

In addition, in some instances, particularly when a fertilizer is an active ingredient, the direct contact of the ORTHENE® insecticide with the fertilizer (or fungicide, herbicide or other insecticide) may chemically degrade the ORTHENE® or vice versa, thereby detracting from the desired activity of the pellet. In such instance each of the active ingredients may be pelletized separately and then blended thereby retaining the stability of each of the active ingredients. For example, KOCIDE TM (copper hydroxide) is not chemically compatible with ORTHENE® and therefore first, KOCIDE TM/Unithox TM 480 pellets may be made into a stable combination, then it is combined with ORTHENE® pellets to form a stable physical insecticide/fungicide formulation. Other fungicides include SPOTLESS TM, FOLPET TM, CAPTAN TM, etc. Herbicides which may be utilized include DEURINOL TM, DURNOL TM, ODRAM, SURFLAN TM, BENCHMARK TM, SELECT TM, etc. Fertilizers include various formulations of NPK fertilizers such as 23-19-17, etc.

In some instances, the physical dry mixture from which the pellets are formed will need to be intimately mixed by evaporation from a solution. For example, ORTHENE® can be protected by a surfactant by first mixing ORTHENE® and a surfactant such as Unithox TM 480 (typically 1:4 ratio) to form a solution in methylene chloride, alcohol, or water. By evaporation of the solvent, the remaining solid may be ground and sieved to an appropriate size (such as 20 mesh). Then the dry powder may be mixed with a solid fertilizer (such as 23-19-17) and pelletized as described above. In this instance the ORTHENE® is protected from the fertilizer by the surfactant.

In the most preferred embodiment according to the present invention the pellets are made by forming a dry, extrudable mixture of the solid technical insecticide composition and the other active ingredients, optionally containing other dry additives described above. The dry ingredients should be ground or provided in a powdered form. In some instances a diluent such as ammonium sulfate will also be utilized usually in an amount less than about 5% and usually around 1% by weight of the total composition. No solvent is added to this composition. However, it is realized that many commercial versions of surfactants contain small amounts (typically about 2% by weight of the surfactant) of moisture. The presence of such moisture is not deleterious to the preparation of the pellet, and the pellet may be later dried, if desired.

As the extrusion product exits the extruding orifice, the product is cut to appropriate size, usually about 3 mm to 10 mm in length. Useful pellets will be extrudates of about 3 mm to 25 mm in length with diameters from about 1.5 mm to 7 mm. Spherical pellets are also useful having diameters of about 1 mm to 5 mm.

EXAMPLE 1

In a Hobart (C-147) mixer 171g of ASANA TM tech (75%) insecticide was added slowly to 243g Celatom TM MN-47 diatomaceous earth. After mixing for 15 minutes 165g of Morwet TM D-425, 15g of Morwet TM EFW (dispersants) were added. This was mixed with 210g Unithox TM 480 (surfactant), 2196g ORTHENE® Tech (98%) and 1.5g of an anti-foam agent (Antifoam A). The mixture was screened to break-up lumps of the insecticides, then extruded into pellets.

EXAMPLE 2

A pre-mix consisting of 177g. SPOTLESS TM Tech (81%), 165g. Morwet TM D-425 and 45g. Morwet TM EFW were mixed in a Hobart mixer. This pre-mix was then mixed with 2463g ORTHENE® Tech (98%), 150g Unithox TM 480 and 1.5g Antifoam A. The mixture was extruded into pellets at about 100° F.

EXAMPLE 3

In a Hobart mixer 210 DIBROM TM (insecticide) was added to 300g Celatom TM and mixed for 15 minutes. This premix was then mixed with 2100g ORTHENE® Tech (98%), 165g Morwet TM D-425, 15g Morwet TM EFW, 210g Unithox TM 480 and 1.5g Antifoam A. The mixture was extruded into pellets at about 91° F.

EXAMPLE 4

To a pre-mix containing 2700g Fertilizer 23-19-17 and 240g Unithox TM 480 were added 60g ORTHENE® Tech (97%) and 1.5g Antifoam A. The mixture was extruded to 3/32" pellets in a California Pellet Mill, then dried.

EXAMPLE 5

A pre-mix of 60g ORTHENE® Tech (97%) and 240g Unithox ™ 480 was ground to a powder, then methylene chloride was added and the mixture was stirred until uniform. The methylene chloride was evaporated, the solids were ground and dried, then placed in a Hobart mixer. To the mixer 2700g of Fertilizer 23-19-17 was added, followed by 1.5g Antifoam A. The mixture was extruded into pellets at a die temperature of about 95.F into 3/32" pellets, then dried.

What is claimed is:

1. A method for preparing insecticidal pellets comprising i) a compound or mixture of compounds of the formula:

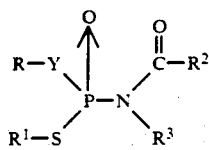

where R and $R^1$ individually are alkyl, alkenyl or alkynyl of up to 6 carbon atoms, $R^3$ is hydrogen or alkyl of 1-6 carbon toms, $R^2$ is hydrogen, alkyl of 1-18 carbon atoms, cycloalkyl of 3-8 carbon atoms, alkenyl of 2-18 carbon atoms or alkynyl of 3-18 carbon atoms, and Y is oxygen or sulfur; ii) a second active ingredient selected from the group consisting of fungicides, herbicides, fertilizers and other insecticides; comprising the steps of (a) forming an extrudable mixture comprising said compound and said second active ingredient;

(b) forming said pellets by extrusion of said mixture extrudable and cutting the extrudate.

2. A method according to claim 1 wherein R and $R^1$ are independently methyl, ethyl, allyl or alkenyl; $R^2$ is H or alkyl; $R^3$ is hydrogen and Y is oxygen.

3. A method according to claim 2 wherein R, $R^1$, and $R^2$ are methyl; $R^3$ is hydrogen.

4. A method according to claim 1 wherein said second active ingredient comprises an insecticide.

5. A method according to claim 4 wherein said extrudable mixture further comprises a solid dispersant, wetting agent and/or surfactant.

6. A method according to claim 4 wherein said insecticide comprises a solid pyrethroid.

7. A method according to claim 4 wherein said insecticide comprises a liquid pyrethroid absorbed in a solid inert carrier.

8. A method according to claim 5 wherein said step (a) comprises mixing said second active ingredient with a surfactant to form surfactant-coated particles of said second active ingredient, and mixing said compound with said surfactant-coated particles.

9. A method according to claim 7 wherein said solid inert carrier comprises diatomaceous earth.

10. A method for preparing solid insecticidal pellets comprising (i) a compound or mixture of compounds of the formula:

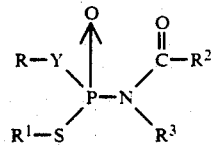

where R and R1 individually are alkyl, alkenyl or alkynyl of up to 6 carbon atoms, R3 is hydrogen or alkyl of 1-6 carbon atoms, R2 is hydrogen, alkyl of 1-18 carbon toms, cycloalkyl of 3-8 carbon atoms, alkenyl of 2-18 carbon atoms or alkynyl of 3-18 carbon atoms and Y is oxygen or sulfur; and (ii) a second active ingredient selected from the group consisting of fungicides, herbicides, fertilizers and other insecticides; comprising the steps of:

(a) forming a suspension or solution containing said compound and a dispersant, wetting agent and/or surfactant;

(b) evaporating the solvent from said solution or dispersion;

(c) dividing the remaining solids into particles; and (d) mixing said particles with said second active ingredient and forming the resultant mixture into pellets.

11. A method according to claim 10 wherein said second active ingredient comprises a solid fertilizer.

* * * * *

UNITED STATES PATENT AND TRADEMARK OFFICE
CERTIFICATE OF CORRECTION

PATENT NO. : 5,075,058

DATED : December 24, 1991

INVENTOR(S) : Chan, Hasse, Satre, and Trusler

It is certified that error appears in the above-identified patent and that said Letters Patent is hereby corrected as shown below:

Column 1, line 51: ...XXS to the crop...should read
...xxS to the crop...

Column 7, line 28: ...carbon toms, $R^2$...should read
...carbon atoms, $R^2$...

Column 8, line 30: ...toms, cyclolkyl... should read
...atoms, cycloalkyl...

Signed and Sealed this

Twentieth Day of July, 1993

Attest:

MICHAEL K. KIRK

*Attesting Officer*    *Acting Commissioner of Patents and Trademarks*